US012765797B2

(12) United States Patent
Van Niekerk et al.

(10) Patent No.: US 12,765,797 B2
(45) Date of Patent: Oct. 20, 2026

(54) IMPEDANCE-BASED NAVIGATION OF SHEATH

(71) Applicant: Biosense Webster (Israel) Ltd., Yokneam (IL)

(72) Inventors: Pieter Emmelius Van Niekerk, Rancho Santa Margarita, CA (US); Amar Patel, Irvine, CA (US); Babak Ebrahimi, Lake Forest, CA (US); Juan Rodriguez Soto, Irvine, CA (US); Jamie Henriquez, Irvine, CA (US); Mohammad Abbas, Orange, CA (US); Danielle Sheppard, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 344 days.

(21) Appl. No.: 18/447,766

(22) Filed: Aug. 10, 2023

(65) Prior Publication Data

US 2025/0049345 A1 Feb. 13, 2025

(51) Int. Cl.
*A61B 5/06* (2006.01)
*A61B 18/00* (2006.01)
*A61B 18/14* (2006.01)

(52) U.S. Cl.
CPC .......... *A61B 5/063* (2013.01); *A61B 18/1492* (2013.01); *A61B 2018/00357* (2013.01);
(Continued)

(58) Field of Classification Search
CPC ... A61B 5/063; A61B 5/0538; A61B 18/1492; A61B 2018/00357; A61B 2018/00577;
(Continued)

(56) References Cited

U.S. PATENT DOCUMENTS 5,391,199 A 2/1995 Ben-Haim
5,443,489 A 8/1995 Ben-Haim
(Continued)

FOREIGN PATENT DOCUMENTS

WO WO-2017219015 A1 * 12/2017 ........... H01Q 1/2216

OTHER PUBLICATIONS

Extended European Search Report and Opinion dated Sep. 25, 2024, from corresponding European Application No. 24193765.5.
(Continued)

*Primary Examiner* — Beverly M Flanagan

(57) ABSTRACT

A sheath is presented having an electrically conducting region providing a low impedance path through the sheath wall. The electrically conducting region is configured to conduct electrical current between an impedance-based tracking electrode of an intralumenal catheter and body patch electrodes of an impedance-based tracking system when the impedance-based tracking electrode is adjacent the conducting region. The impedance-based tracking system is configured to determine a location of the electrically conducting region, and thereby the distal end of the sheath, based on ratios of electrical current at the body patch electrodes. The electrically conducting region can include irrigation perforations so that saline acts as an electrical conduit of the conducting region. Additionally, or alternatively, the electrically conducting region can include an electrically conductive material configured to act as an electrical conduit through the sheath wall.

16 Claims, 7 Drawing Sheets

(52) U.S. Cl.
CPC ............... *A61B 2018/00577* (2013.01); *A61B 2018/00839* (2013.01); *A61B 2218/002* (2013.01)

(58) Field of Classification Search
CPC ........... A61B 2018/00839; A61B 2018/00875; A61B 2218/002; A61B 2034/2053; A61B 2034/2051; A61B 2034/2072; A61B 2034/2046; A61B 34/20
USPC ........................................................... 606/41
See application file for complete search history.

(56) References Cited

U.S. PATENT DOCUMENTS

| | | | | |
|---|---|---|---|---|
| 5,558,091 | A | 9/1996 | Acker et al. | |
| 5,738,096 | A | 4/1998 | Ben-Haim | |
| 6,172,499 | B1 | 1/2001 | Ashe | |
| 6,239,724 | B1 | 5/2001 | Doron et al. | |
| 6,332,089 | B1 | 12/2001 | Acker et al. | |
| 6,484,118 | B1 | 11/2002 | Govari | |
| 6,618,612 | B1 | 9/2003 | Acker et al. | |
| 6,690,963 | B2 | 2/2004 | Ben-Haim et al. | |
| 6,788,967 | B2 | 9/2004 | Ben-Haim et al. | |
| 6,892,091 | B1 | 5/2005 | Ben-Haim et al. | |
| 7,536,218 | B2 | 5/2009 | Govari et al. | |
| 7,756,576 | B2 | 7/2010 | Levin | |
| 7,848,787 | B2 | 12/2010 | Osadchy | |
| 7,869,865 | B2 | 1/2011 | Govari et al. | |
| 8,456,182 | B2 | 6/2013 | Bar-Tal et al. | |
| 9,907,480 | B2 | 3/2018 | Basu et al. | |
| 10,398,347 | B2 | 9/2019 | Pressman et al. | |
| 2015/0126895 | A1* | 5/2015 | Lichtenstein | A61B 5/6852 600/547 |
| 2018/0036078 | A1 | 2/2018 | Ditter | |
| 2018/0056038 | A1 | 3/2018 | Aujla | |
| 2020/0015876 | A1 | 1/2020 | Chou et al. | |
| 2020/0038101 | A1 | 2/2020 | Tobey et al. | |
| 2020/0155845 | A1 | 5/2020 | Bonner et al. | |

OTHER PUBLICATIONS

Edward Koźluk et al., "First experience with left atrial arrhythmia ablation using a bidirectional steerable transseptal sheath (Vizigo) visible in the CARTO system as a method to reduce fluoroscopy", European Journal of Translational and Clinical Medicine 2020;3(2):18-21.

Website: https://www.jnjmedtech.com/en-US/product/carto-vizigo-bi-directional-guiding-sheath, "Carto Vizigo(R) Bi-Directional Guiding Sheath", published by Biosense Webster, Inc., last updated Jan. 5, 2021, accessed on Aug. 10, 2023.

Exam Report under Article 94(3) EPC dated Mar. 26, 2026, from corresponding European Application No. 24193765.5.

* cited by examiner

IMPEDANCE-BASED NAVIGATION OF SHEATH

BACKGROUND

Tracking the position of intrabody objects, such as sensors, tubes, catheters, dispensing devices, and implants, is required for many medical procedures. Well-established, highly accurate systems for determining the position of an intrabody object have been developed based on magnetic field sensing. These systems utilize sensors affixed to the intrabody object to measure the relative strengths of externally-generated magnetic fields and to derive from these measurements the position of the object. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091 each of which are incorporated by reference herein.

Position sensing systems have also been developed which utilize impedance-based measurements. In such systems, impedance is measured between electrodes affixed to the intrabody object and electrodes placed on the body surface. The systems then derive the position of the intrabody object from the impedance measurements. Details of the impedance-based location tracking technology are described in U.S. Pat. Nos. 7,536,218; 7,756,576; 7,848,787; 7,869,865; and 8,456,182 each of which are incorporated by reference herein and attached in the Appendix hereto.

Regions of cardiac tissue can be mapped by a catheter to identify abnormal electrical signals. Cardiac tissue may be ablated to interrupt the abnormal electrical signals. Electrophysiology mapping may include the use of sensing electrodes on a catheter configured to monitor electrical signals within the cardiovascular system to pinpoint the location of aberrant conductive tissue sites that are responsible for the arrhythmia. Examples of an EP mapping system are described in U.S. Pat. No. 5,738,096, incorporated herein by reference. Examples of EP mapping catheters are described in U.S. Pat. No. 9,907,480, U.S. Patent Pub. No. 2018/0036078, and U.S. Patent Pub. No. 2018/0056038, each of which are incorporated by reference herein.

In addition to using EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, Calif.

SUMMARY

A sheath is presented herein which can have radial perforations in a sheath wall approximately 1 to 3 centimeters (cm) from the distal end of the sheath. The perforations can be large enough to allow saline to perfuse during sheath irrigation. The perforations can extend approximately 1 to 2 millimeters (mm) along the length of the sheath. The sheath is configured such that the perforations act as a conductive conduit to an impedance-based tracking electrode of a catheter positioned within a lumen of the sheath. When the impedance-based tracking electrode is positioned adjacent or near the perforations. The impedance-based tracking electrode can be positioned on a shaft of the catheter. For instance, the impedance-based tracking electrode can include an inferior vena cava (IVC) electrode, the most proximal electrode of a focal catheter such as SMARTTOUCH® SF by Biosense Webster. When the impedance-based tracking electrode is positioned adjacent to or near the perforations, electrical currents injected from the catheter electrode will conduct primarily through the perforations. A control unit of an impedance based tracking system can calculate the position of the perforations of the sheath based on ratios of electrical currents between the impedance-based tracking electrode and body patches (e.g. six body patches). This calculation allows for visualization of the sheath itself, instead of only the impedance-based tracking electrode traveling through the sheath. Alternatively, instead of perforations, a small band of conductive material can be placed on sheath to allow electrical current to pass through the sheath wall. This conductive material can be polymeric or metallic in nature and make up the full section of the sheath in that region, and/or it can include conductive fibers or rivets (polymeric or metallic) that act as passthrough channels for the ACL current.

An exemplary guiding sheath can include a tubular shaft extending along a longitudinal axis between a proximal end and a distal end. The tubular shaft can have a lumen therethrough and a tubular wall circumscribing the lumen. A predetermined tubular wall region can be configured to provide an electrically conductive path through the tubular wall of the tubular shaft. The predetermined tubular wall region can be disposed proximate the distal end of the tubular shaft.

An exemplary impedance-based tracking system can include a guiding sheath, a medical probe, a plurality of body patch electrodes, and a control unit. The guiding sheath can include a first tubular shaft having a lumen therethrough and a predetermined tubular wall region disposed approximate a distal end of the first tubular shaft. The predetermined tubular wall region can be configured to provide an electrically conductive path through the predetermined tubular wall region. The medical probe can include a second tubular shaft configured to be translated through the lumen of the first tubular shaft. The medical probe can further include a tracking electrode coupled to the second tubular shaft. The plurality of body patch electrodes can be configured to be in contact with skin of a patient. The control unit can be configured to determine a position of the predetermined tubular wall region based at least in part on electrical signals between the tracking electrode and the plurality of body patch electrodes.

An exemplary method of impedance tracking of a guiding sheath within a patient can include the following steps performed in a variety of orders and with interleaving steps as understood by a person skilled in the pertinent art. The method can include passing electrical current signals between a probe electrode of a medical probe and a plurality of body patch electrodes, the probe electrode being disposed within a lumen of the guiding sheath within the patient, and the plurality of body patch electrodes being in contact with skin of the patient. The method can include determining a position of a distal portion of the guiding sheath based at least in part on the electrical current signals.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements. The figures depict one or more implementations of the inventive devices, by way of example only, not by way of limitation.

DETAILED DESCRIPTION

Figure 1:
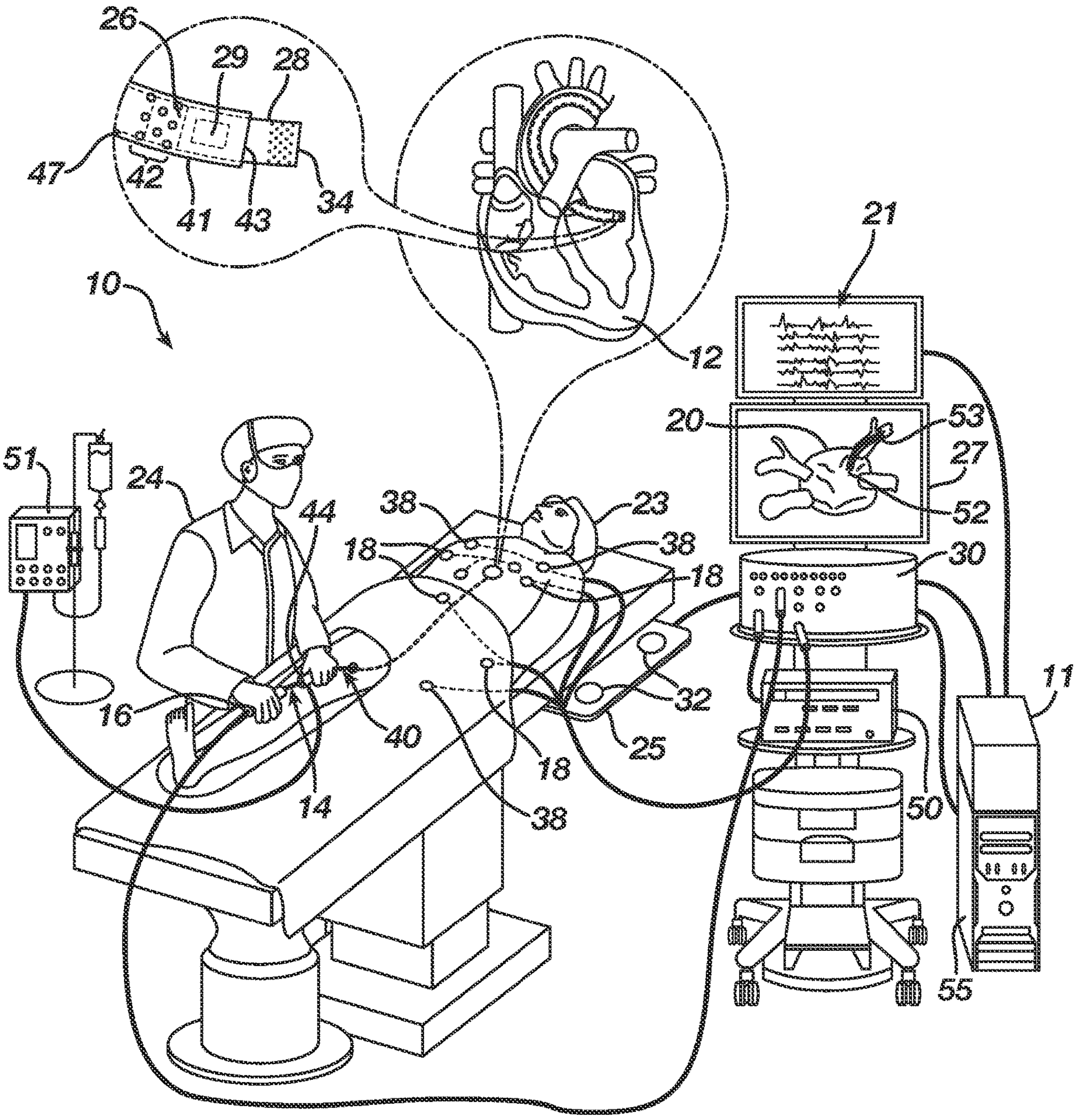
FIG. 1 is an illustration of an example catheter-based electrophysiology mapping and ablation system.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives, and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%.

In addition, as used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician.

As used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular structure or system may have a tapered or curved outer surface without departing from the scope of the present invention. A tubular structure or system or tube may have a hollow lumen, a solid core, or a combination thereof.

As used herein, the terms "sheath" and "guiding sheath" refer to an elongated intravascular device with a hollow tubular shaft configured to deliver one or more medical probes to a treatment site within a body of a patient. A sheath or guiding sheath is sized based on an inner diameter of a lumen of the hollow tubular shaft (e.g. as measured in units of French). A sheath or guiding sheath may or may not be steerable.

As used herein, the term "catheter" refers to an elongated intravascular device which may be configured as a therapeutic and/or diagnostic medical probe. A catheter is sized based on an outer diameter of an elongated tubular body (e.g. as measured in units of French). A catheter may be delivered through a compatible sheath having a size that is compatible with the size of the catheter.

Alternative apparatus and system features and alternative method steps are presented in example embodiments herein. Each given example embodiment presented herein can be modified to include a feature and/or method step presented with a different example embodiment herein where such feature and/or step is compatible with the given example as understood by a person skilled in the pertinent art as well as where explicitly stated herein. Such modifications and variations are intended to be included within the scope of the claims.

FIG. 1 is an illustration showing an example catheter-based electrophysiology mapping and ablation system 10. The system 10 includes multiple catheters, which are percutaneously inserted by a physician 24 through the patient's vascular system into a chamber or vascular structure of a heart 12. Typically, a guiding sheath 40 is inserted into the left or right atrium near a desired location in the heart 12. Thereafter, a plurality of catheters can be inserted into the guiding sheath 40 to arrive at the desired location. The plurality of catheters may include catheters dedicated for sensing Intracardiac Electrogram (IEGM) signals, catheters dedicated for ablating and/or catheters configured for both sensing and ablating. An example catheter 14 is illustrated herein. The physician 24 brings a distal electrode 34 of the catheter 14 into contact with the heart wall for sensing and/or ablation of a target site in the heart 12.

The catheter 14 optionally includes a magnetic-based position sensor 29 embedded in a distal portion 28 of the catheter 14 for tracking position and orientation of the distal portion 28. Preferably, the magnetic-based position sensor 29 includes three magnetic coils for sensing three-dimensional (3D) position and orientation.

The magnetic-based position sensor 29 may be operated together with a location pad 25 including a plurality of magnetic coils 32 configured to generate magnetic fields in a predefined working volume. Real time position of the distal portion 28 of the catheter 14 may be tracked based on magnetic fields generated with the location pad 25 and sensed by the magnetic-based position sensor 29. Details of the magnetic-based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091 incorporated by reference herein.

The illustrated system 10 includes one or more electrode patches 38 positioned for skin contact on the patient 23 to establish location reference for location pad 25 as well as impedance-based tracking of one or more impedance-based tracking electrodes 26. For impedance-based tracking, electrical current is directed toward the impedance-based tracking electrode(s) 26 and sensed at electrode skin patches 38 so that the location of each electrode 26 can be triangulated via the electrode patches 38. Details of the impedance-based location tracking technology are described in U.S. Pat. Nos. 7,536,218; 7,756,576; 7,848,787; 7,869,865; and 8,456,182 incorporated by reference herein and attached in the Appendix hereto. Instead of relying on the electrode patches 38, the catheter can utilize existing impedance sensing electrode 39' on the sheath 40 (FIG. 4B) similar to that of the impedance sensing electrodes provided on Biosense Webster Vizigo Sheath Introducer product (shown here https://www.jnjmedtech.com/en-US/product/carto-vizigo-bi-directional-guiding-sheath) and described in the article titled "FIRST EXPERIENCE WITH LEFT ATRIAL ARRHYTHMIA ABLATION USING A BIDIRECTIONAL STEERABLE TRANSSEPTAL SHEATH (VIZIGO) VISIBLE IN THE CARTO SYSTEM AS A METHOD TO REDUCE FLUOROSCOPY" published by the EUROPEAN JOURNAL OF TRANSLATIONAL AND CLINICAL MEDICINE 2020; 3(2):18-21 with Corresponding author: Edward Koźluk, PhD MD, I Chair and Department of Cardiology, Medical University of Warsaw, Edward Koźluk1, Katarzyna Lojewska, Jaroslaw Hiczkiewicz and Available online: www.ejtem.gumed.edu.pl. A copy of the aforementioned article is incorporated by reference herein and attached in the Appendix hereto. In some embodiments, the sensing electrodes 39' are optional, and location of the sheath 40 can be determined without the sensing electrodes 39'.

The guiding sheath 40 can include a predetermined tubular wall region 42, positioned at a predetermined location in relation to a distal end 43 of the sheath in the wall of the tubular shaft 47 of the guiding sheath 40. The predetermined tubular wall region which includes a low-impedance path through the wall of the guiding sheath 40. When an impedance-based tracking electrode 26 of the catheter 14 is positioned adjacent the predetermined tubular wall region 42 of the guiding sheath 40, electrical current is directed toward the impedance-based tracking electrode 26, through the predetermined tubular wall region 42, and sensed at the electrode skin patches 38 so that the location of the predetermined tubular wall region 42 can be triangulated via the electrode patches 38 with systems and methods disclosed in in U.S. Pat. Nos. 7,536,218; 7,756,576; 7,848,787; 7,869,865; and 8,456,182 incorporated by reference herein and attached in the Appendix hereto, variations thereof, and alternatives thereto, as understood by a person skilled in the pertinent art.

The predetermined tubular wall region 42 can be disposed about 1 centimeter from the distal end 43 of the tubular shaft of the sheath 40 and extending along the tubular shaft for about 1 millimeter to 2 millimeters.

The predetermined tubular wall region 42 can include various features to facilitate electrical conduction through the tubular wall at the predetermined tubular wall region 42. For instance, the predetermined tubular wall region can include pores sized to permit flow of saline from the lumen through the tubular wall of the tubular shaft, an electrically conductive band coupled to the tubular wall of the guiding sheath and configured to conduct electrical current between the lumen and an external environment of the tubular shaft, electrically conductive rivets extending through the tubular wall of the guiding sheath, electrically conductive fibers embedded in the tubular wall of the guiding sheath and configured to conduct electrical current between the lumen and an external environment of the tubular shaft, combinations thereof, or variations thereof in various combinations.

The guiding sheath 40 further includes a sheath handle 44 coupled to a proximal end of the tubular shaft 47. The handle 44 can be configured to deflect the distal portion 41 of the tubular shaft 47 of the guiding sheath 40. The guiding sheath 40 can further include an irrigation port configured to connect to an irrigation system 51 to provide irrigation fluid to the lumen of the guiding sheath 40. When the predetermined tubular wall region 42 includes pores, the flow of saline through the pores can provide an electrically conductive path through the tubular wall of the tubular shaft 47 of the guiding sheath 40. The distal portion 41 of the guiding sheath 40 can be located based on impedance signals through the saline solution in the pores of the predetermined tubular wall region 42.

The tubular shaft 47 of the guiding sheath 40 can lack an active position sensor. Impedance based tracking based on electrical signals through the predetermined tubular wall region 42 can be sufficient to track the distal portion 41 of the guiding sheath 40. The guiding sheath 40 can further lack an electrical port. Impedance based tracking based on electrical signals through the predetermined tubular wall region 42 can be sufficient to track the distal portion 41 of the guiding sheath 40 without any electrical signals being transmitted along the length of the tubular shaft 47.

The impedance-based tracking electrode(s) 26 may be multi-functional and may additionally be configured for sensing and/or ablation.

A recorder 11 displays electrograms 21 captured with body surface ECG electrodes 18 and intracardiac electrograms (IEGM) captured with one or more electrodes 26, 34 of the catheter 14. The recorder 11 may include pacing capability for pacing the heart rhythm and/or may be electrically connected to a standalone pacer.

The system 10 can include an ablation energy generator 50 that is adapted to conduct ablative energy to the distal electrode 34 of the catheter 14. Energy produced by the ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

A patient interface unit (PIU) 30 is an interface configured to establish electrical communication between catheters, electrophysiological equipment, power supply and a workstation 55 for controlling operation of system 10. Electrophysiological equipment of the system 10 may include for example, multiple catheters, a location pad 25, body surface ECG electrodes 18, electrode patches 38, an ablation energy generator 50, and a recorder 11. Optionally and preferably, the PIU 30 includes processing capability for implementing real-time computations of location of the catheters and for performing ECG calculations.

The workstation 55 includes memory, processor unit with memory or storage with appropriate operating software loaded therein, and user interface capability. The workstation 55 can be configured to provide multiple functions, optionally including (1) modeling the endocardial anatomy in three-dimensions (3D) and rendering the model or an anatomical map 20 for display on a display device 27; (2) displaying on the display device 27 activation sequences (or other data) compiled from recorded electrograms 21 in representative visual indicia or imagery superimposed on the rendered anatomical map 20; (3) displaying a graphical representation 53 of the sheath 40 and/or a graphical representation 52 of the catheter 14, with real-time location and orientation within the heart chamber; and (4) displaying on the display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

Figure 2:
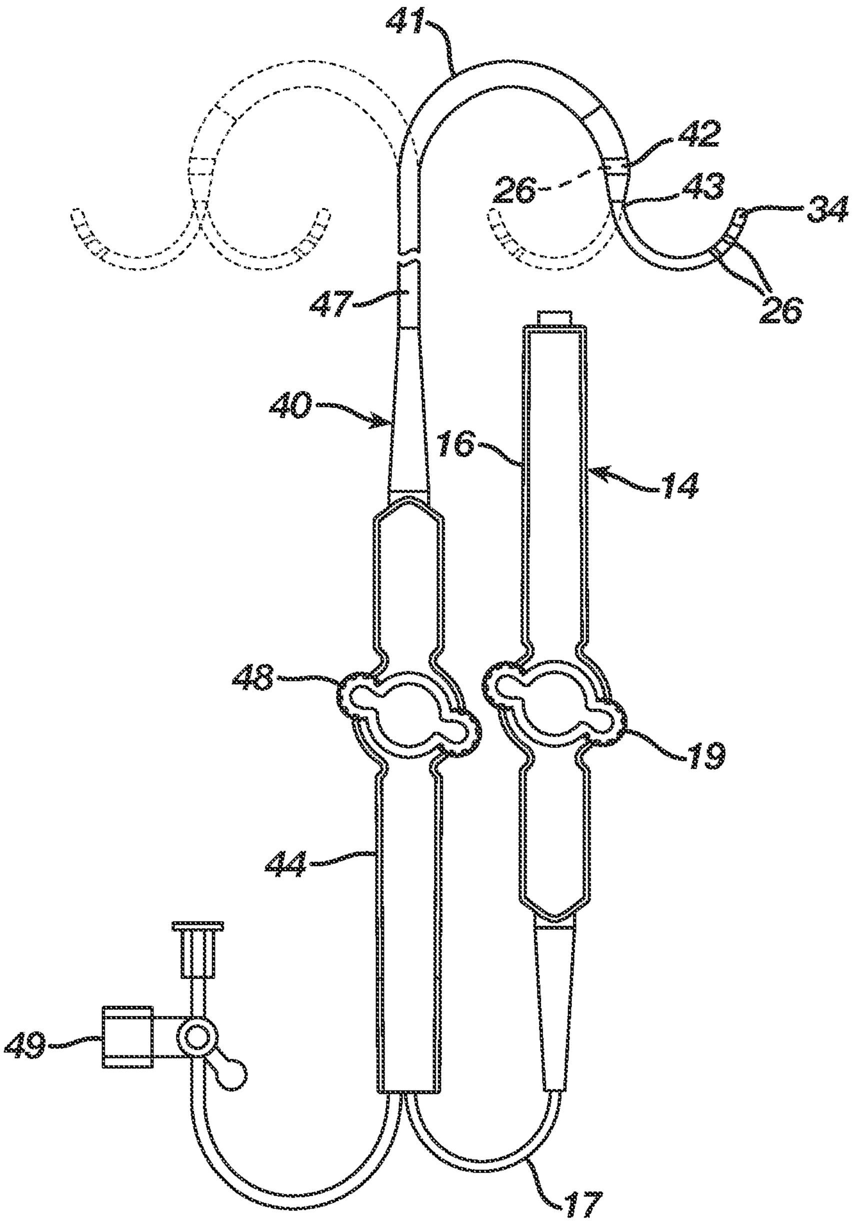
FIG. 2 is an illustration of an exemplary sheath and catheter.

FIG. 2 is an illustration of an exemplary guiding sheath 40 and catheter 14. The guiding sheath 40 includes handle 44, an irrigation port 49 extending proximally from the handle 44, and a tubular shaft 47 extending distally from the handle 44. The tubular shaft 47 has a distal portion 41 and a predetermined tubular wall region 42 in the distal portion 41. The handle 44 includes a knob 48 that can be manipulated to deflect the distal portion 41 of the tubular shaft 47 as illustrated.

The catheter 14 includes a handle 16 and a catheter shaft 17 extending distally from the catheter handle 16. The catheter shaft 17 includes impedance-based tracking electrodes 26 and a distal electrode 34. A distal portion of the catheter shaft 17 can be deflected by manipulation of a catheter knob 19 on the catheter handle 16.

The guiding sheath 40 includes a lumen therethrough, through which the shaft of the catheter 14 can be translated. As illustrated, the catheter shaft can extend through the handle 44 of the guiding sheath 40, through the tubular shaft 47 of the guiding sheath, and extending from a distal end 43 of the guiding sheath 40. When the impedance-based tracking electrodes 26 of the catheter 14 are aligned with the predetermined tubular wall region 42, an electrically conductive path exists through the predetermined tubular wall region 42 to the impedance-based tracking electrodes 26.

Figure 3A:
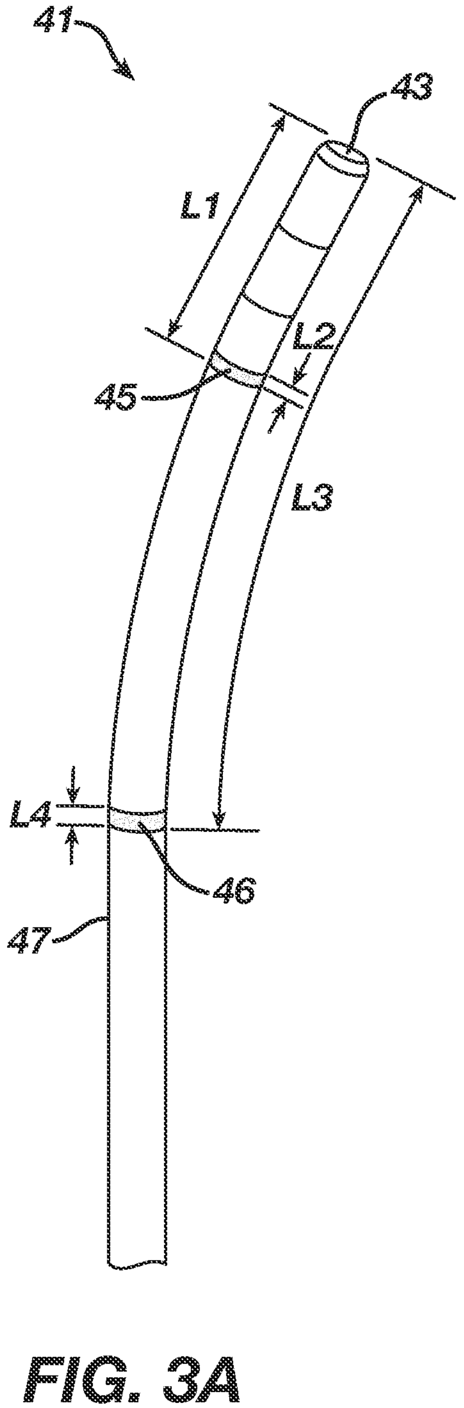
FIG. 3A is an illustration of a distal portion of the sheath.

FIG. 3A is an illustration of a distal portion 41 of the sheath 40. The tubular shaft 47 includes a proximal conducting region 46 and a distal conducting region 45. Each conducting region 45, 46 is configured similar to the predetermined tubular wall region 42 illustrated in FIGS. 1, 2, 4A, 4B, 5, and 6A through 6D. Each conducting region 45, 46 can respectively include pores sized to permit flow of saline from the lumen through the tubular wall of the tubular shaft, an electrically conductive band coupled to the tubular wall of the guiding sheath and configured to conduct electrical current between the lumen and an external environment of the tubular shaft, electrically conductive rivets extending through the tubular wall of the guiding sheath, electrically conductive fibers embedded in the tubular wall of the guiding sheath and configured to conduct electrical current between the lumen and an external environment of the tubular shaft, combinations thereof, or variations thereof in various combinations. Each conducting region 45, 46 can otherwise be configured to provide an electrically conductive path through the tubular wall of the tubular shaft 47 of the guiding sheath 40.

The distal conducting region 45 can be disposed a predetermined distance L1 from the distal end 43 of the guiding sheath 40. The proximal conducting region 46 can be disposed a predetermined distance L3 from the distal end 43 of the guiding sheath 40. The distal conducting region 45 can be shaped as a ring, with a length L2, that circumscribes the tubular shaft 47. The proximal conducting region 46 can be shaped as a ring, with a length L4, that circumscribes the tubular shaft 47.

Figure 3B:
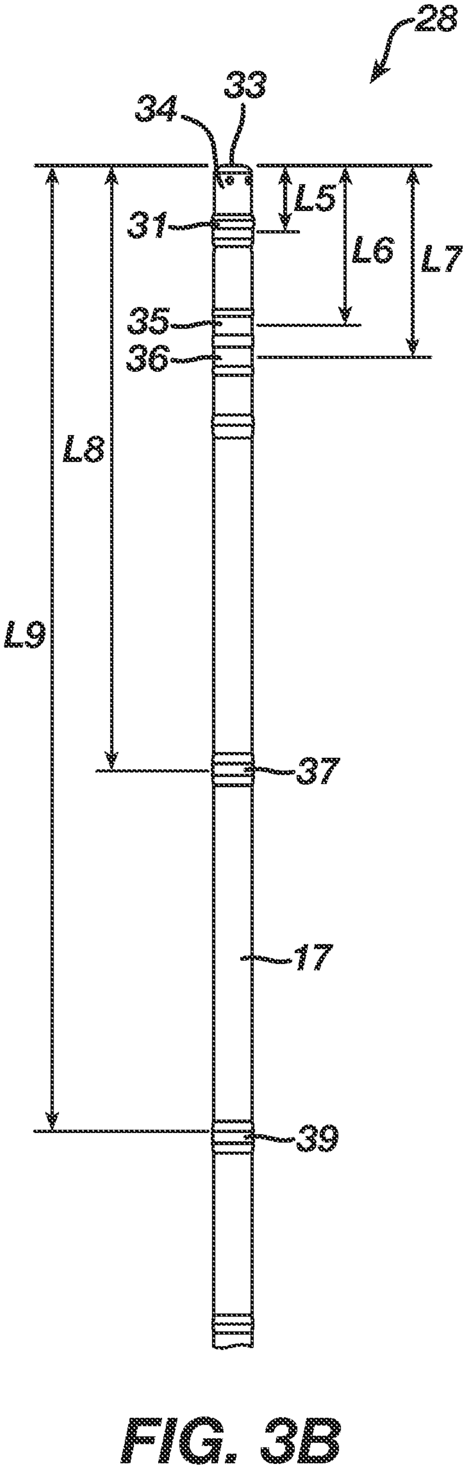
FIG. 3B is an illustration of a distal portion of the catheter.

FIG. 3B is an illustration of a distal portion 28 of the catheter 14. The catheter 14 includes ring electrodes 31, 35, 36, 37, 39. Each of the ring electrodes can be configured as an impedance tracking electrode similar to impedance-based tracking electrode 26 illustrated in FIGS. 1, 2, 4A and 4B. The catheter 14 can include a distal ring electrode 31 disposed a first distance L5 from the distal end 33 of the catheter 14, a second ring electrode 35 disposed a second distance L6 from the distal end 33 of the catheter 14, a third ring electrode 35 disposed a third distance L7 from the distal end 33 of the catheter 14, a fourth ring electrode 35 disposed a fourth distance L8 from the distal end 33 of the catheter 14, and a fifth ring electrode 35 disposed a fifth distance L9 from the distal end 33 of the catheter 14.

As illustrated in FIGS. 3A and 3B, the guiding sheath 40 can include multiple conducting regions 45, 46, and the catheter 14 can include multiple ring electrodes 31, 35, 36, 37, 39. Some, or all, of the ring electrodes 31, 35, 36, 37, 39 can be configured as impedance tracking electrodes. As the catheter 14 is translated distally through the guiding sheath 40, ring electrodes 31, 35, 36, 37, 39 pass through the conducting regions 45, 46. The distances L1, L3 between the conducting regions 45, 46 and the distal end 43 of the guiding sheath 40 and the distances L5, L6, L7, L8, L9 can be configured such that two of the ring electrodes 31, 35, 36, 37, 39 are simultaneously aligned with conducting regions 45, 46 so that the position of the conducting regions 45, 46 can simultaneously be determined by an impedance-based tracking system. The distances L1, L3, L5, L6, L7, L8, L9 can further be configured such that while two of the ring electrodes (e.g. two proximal most electrodes 37, 39) are simultaneously aligned with the conducting regions 45, 46, a third electrode (e.g. one or both of the middle electrodes 35, 36) is positioned distal of the distal end 43 of the guiding sheath 40 and approximate the distal end 43 of the guiding sheath 40 so that the location of the conducting regions 45, 46 and the location of the distal end 43 of the guiding sheath 40 can be determined by the impedance-based tracking system. The curvature of the distal portion 41 of the guiding sheath 40 can be determined based on the location of the conducting regions 45, 46 and the distal end 43. The impedance-based tracking system can further determine the position and curvature of a distal portion of the catheter 14 based on location of ring electrodes 31, 35, 36, 37, 39 which are distal of the distal end 43 of the guiding sheath 40.

The catheter 14 as illustrated, is a focal ablation catheter. Examples of a focal ablation catheter include CELSIUS®, NAVISTAR®, THERMOCOOL SMARTTOUCH® SF, THERMOCOOL SMARTTOUCH®, THERMOCOOL®, and THERMOCOOL® RMT by Biosense Webster. Alternatively, the catheter 14 can be another therapeutic or diagnostic catheter configured with at least one impedance-based tracking electrode 26. The catheter 14 can include a linear end effector (as illustrated), a lasso or curved end effector, a basket shaped end effector, a balloon end effector, a ray end effector, variations thereof, or alternative thereto as understood by a person skilled in the art. The end effector of the catheter 14 can include one or more electrodes configured to sense intracardiac electrogram signals. The end effector of the catheter 14 can include one or more electrodes configured to provide electrical signals for radio frequency ablation and/or irreversible electroporation.

As an alternative to the catheter 14, the system 10 (FIG. 1) can be configured to with a medical probe having at least one impedance-based tracking electrode 26. For instance, a dilator having at least one impedance-based tracking electrode 26, or a medical probe having a dilator and at least one impedance-based tracking electrode 26 can be used in place of the catheter 14.

At least one of the predetermined tubular wall regions 45, 46 are preferably disposed about 1 centimeter to about 3 centimeters from the distal end 43 of the tubular shaft 47 of the guiding sheath 40. The lengths L2, L4 of the predetermined tubular wall regions are preferably about 1 millimeter to about 2 millimeters.

Figure 4A:
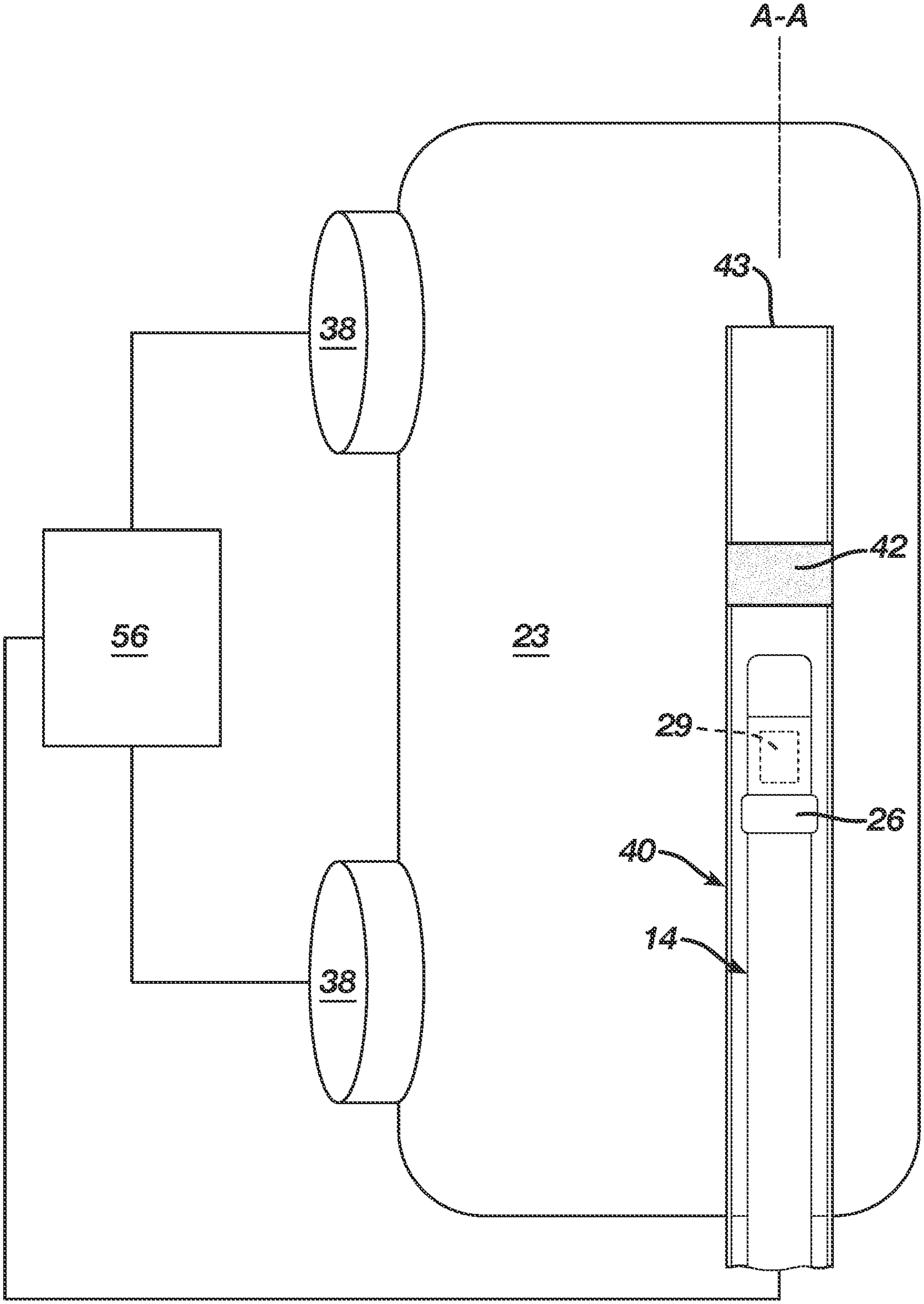
FIG. 4A is an illustration of an impedance-based tracking system in which an impedance-based tracking electrode of the catheter is not adjacent a conducting region of the sheath.

FIG. 4A is an illustration of an impedance-based tracking system in which an impedance-based tracking electrode 26 of the catheter 14 is not adjacent a predetermined tubular wall region 42 of the sheath 40. For the sake of illustration, the catheter 14 includes only one impedance-based tracking electrode 26, and the sheath 40 includes only one predetermined tubular tall region 42. The catheter 14 and/or sheath 40 can alternatively be configured as disclosed in relation to FIGS. 3A and 3B. The catheter 14 is positioned with its tubular body in the tubular body of the guiding sheath 40 so that the tubular bodies of the catheter 14 and the guiding sheath 40 are aligned along the longitudinal axis A-A.

Figure 4B:
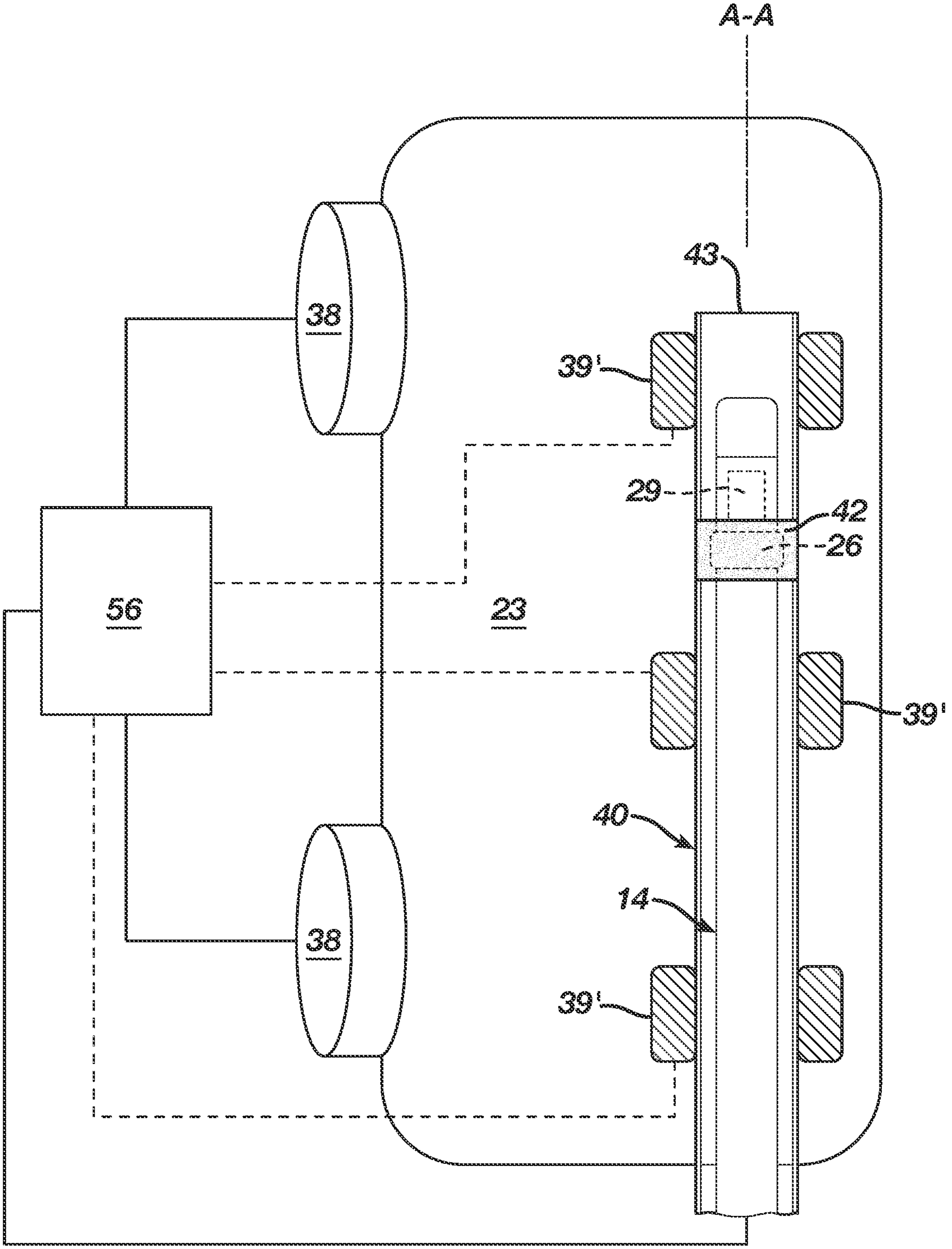
FIG. 4B is an illustration of the impedance-based tracking system in which the impedance-based tracking electrode is adjacent the conducting region of the sheath.

The impedance-based tracking system includes the guiding sheath 40, the catheter 14 (or other suitable medical probe), body patches 38, and a control unit 56. FIGS. 4A and 4B include elements of system 10 illustrated in FIG. 1.

When the impedance-based tracking electrode 26 is not in alignment with the predetermined tubular wall region 42, there is not a direct path for electrical current between the impedance-based tracking electrode 26 and the body patches 38, therefore the impedance between the impedance-based tracking electrode 26 and the body patches 38 is high. It may be difficult or impossible to determine the location of the impedance-based tracking electrode 26 when the impedance-based tracking electrode 26 is not aligned with the predetermined tubular wall region 42.

FIG. 4B is an illustration of the impedance-based tracking system in which the impedance-based tracking electrode 26 is adjacent the predetermined tubular wall region 42 of the guiding sheath 40. When the impedance-based tracking electrode 26 is in alignment with the predetermined tubular wall region 42, electrical current can pass between the body patch electrodes 38 and the impedance-based tracking electrode 26 through the predetermined tubular wall region 42. Additionally, or alternatively, the sensing electrodes 39' can be used in place of body patch electrodes 38. The control unit 56 can be configured to determine a position of the predetermined tubular wall region 42 based at least in part on electrical signals between the tracking electrode 26 and the body patch electrodes 38. The controller can be configured to drive electric currents between the body patch electrodes 38 and the impedance-based tracking electrode 26. The controller can be configured to measure impedance between the impedance-based tracking electrode 26 and the body patch electrodes 38 to determine distance between the impedance-based tracking electrode 26 and each of the body patch electrodes 38 to determine three-dimensional coordinates of the impedance-based tracking electrode 26.

The impedance between the impedance-based tracking electrode 26 and each of the body patch electrodes 38 decreases dramatically as the impedance-based tracking electrode 26 is moved from a misaligned position (e.g. FIG. 4A) into an aligned position (e.g. FIG. 4B). The control unit 56 can be configured to determine that the impedance-based tracking electrode 26 is in alignment with the predetermined tubular wall region 42 by detecting the dramatic decrease in impedance.

When the catheter 14 includes two or more impedance-based tracking electrodes 26 (e.g. ring electrodes 31, 35, 36, 37, 39 illustrated in FIG. 3B), at least one of the impedance-based tracking electrodes can be in a misaligned position (e.g. FIG. 4A) while at least one of the impedance-based tracking electrodes is in alignment with one or more conducting regions of the guiding sheath 40. There can be a higher impedance between the impedance-based tracking electrode(s) in the misaligned position and the body patch electrodes 38 compared to impedance between impedance-based tracking electrode(s) in the aligned position and the body patch electrodes 38. The control unit 56 can be configured to determine which of the impedance-based tracking electrodes are in the aligned position vs. in the misaligned position based on a comparison of impedances between each impedance-based tracking electrode and the body patch electrodes 38. The controller can be configured to determine that those impedance-based tracking electrode(s) having higher impedance are misaligned and those having lower impedance are aligned. The controller can be configured to determine the location of each predetermined tubular wall region based on the position of each impedance-based tracking electrode in the aligned position.

The control unit 56 can be configured to determine a position of the distal end 43 of the tubular shaft of the guiding sheath 40 based at least in part on the position of the predetermined tubular wall region 42.

The control unit 56 can be configured to determine a position and orientation of the distal portion 41 of the guiding sheath 40 in relation to anatomy of the patient. As illustrated in FIG. 1, the system 10 can be configured to generate an anatomical map 20. A graphical representation 52 of the distal portion of the catheter 14 can be superimposed on the anatomical map 20 based on magnetic and/or impedance based tracking of the catheter 14. A graphical representation 53 of the distal portion 41 of the guiding sheath 40 can be superimposed on the anatomical map 20 based on impedance-based tracking of the predetermined tubular wall region 62 (or predetermined tubular wall regions).

The control unit 56 can be configured to determine a position and orientation of the distal portion 41 of the guiding sheath 40 without relying on an active position sensor on the tubular shaft 47 of the guiding sheath 40. The control unit 56 can be configured to determine a position and orientation of the distal portion 41 of a guiding sheath 40 lacking an active position sensor.

The control unit 56 can be configured to determine a position and orientation of the distal portion 41 of the guiding sheath 40 without relying on any electrical signal connection to the guiding sheath 40. The control unit 56 can be configured to determine a position and orientation of the distal portion 41 of a guiding sheath 40 lacking an electrical port.

The illustrated sensing electrodes 39' in FIG. 4B are optional. Additionally, or alternatively, the sensing electrodes 39' can be used in place of, or in addition to, body patch electrodes 38.

Figure 5:
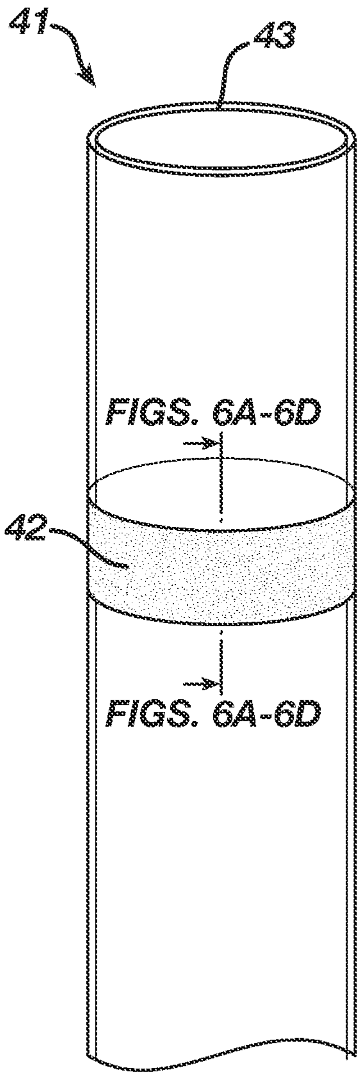
FIG. 5 is an illustration of a distal portion of an exemplary sheath.

FIG. 5 is an illustration of a distal portion 41 of the guide sheath 40.

FIGS. 6A, 6B, 6C, and 6D are cross-sectional illustrations of the distal portion 41 of the guiding sheath 40 as indicated in FIG. 5, showing exemplary configurations of the predetermined tubular wall region 42 configured to provide an electrically conductive path through the tubular wall.

Figure 6A:
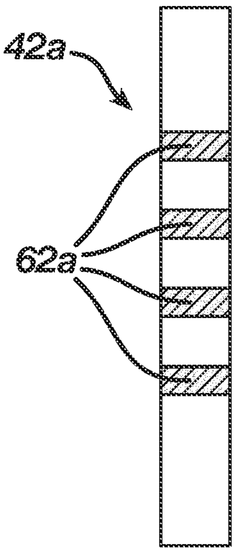
FIGS. 6A, 6B, 6C, and 6D are cross-sectional illustrations of the distal portion of the exemplary sheath as indicated in FIG. 5, showing exemplary configurations of a predetermined tubular wall region configured to provide an electrically conductive path through the tubular wall.

FIG. 6A illustrates a cross-section in which the predetermined tubular wall region 42*a* includes circular pores 62*a* similar to as illustrated in FIG. 1. The pores can allow saline to flow through the lumen of the guiding sheath 40 to provide a conductive path through the tubular wall of the guiding sheath 40. Alternatively, the tubular wall region 42 can include circular plugs filled with electrically conductive material (e.g. conductive polymer or metal) as an alternative to saline.

Figure 6B:
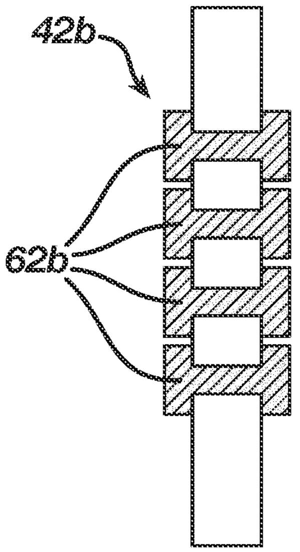

FIG. 6B illustrates a cross-section in which the predetermined tubular wall region 42*b* includes electrically conductive rivets 62*b* extending through a wall of the first tubular shaft. The rivets include an electrically conductive material (e.g. conductive polymer or metal).

Figure 6C:
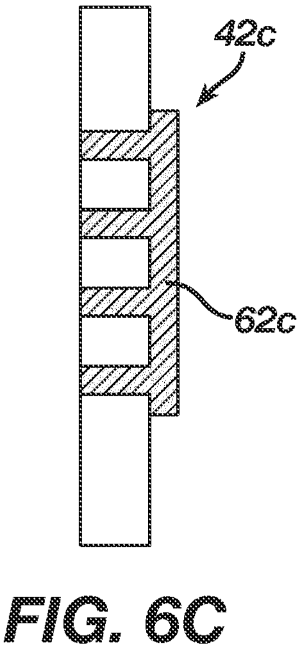

FIG. 6C illustrates a cross-section in which the predetermined tubular wall region 42*c* includes an electrically conductive band 62*c* or ring coupled to the wall of the tubular shaft of the guiding sheath 40 and configured to conduct electrical current between the lumen and an external environment of the tubular shaft.

Figure 6D:
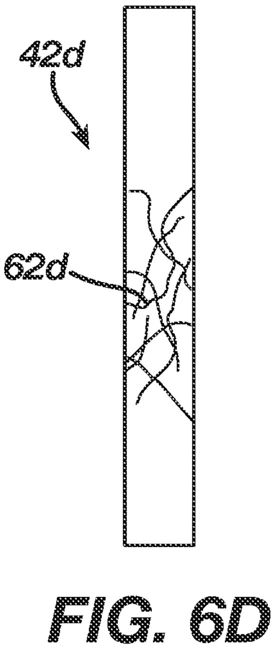

FIG. 6D illustrates a cross-section in which the predetermined tubular wall region 42*d* includes electrically conductive fibers 62*d* embedded in a wall of the tubular shaft of the guiding sheath 40. The electrically conductive fibers 62*d* are configured to conduct electrical current between the lumen of the tubular shaft of the guiding sheath 40 and an external environment of the tubular shaft.

Figure 7:
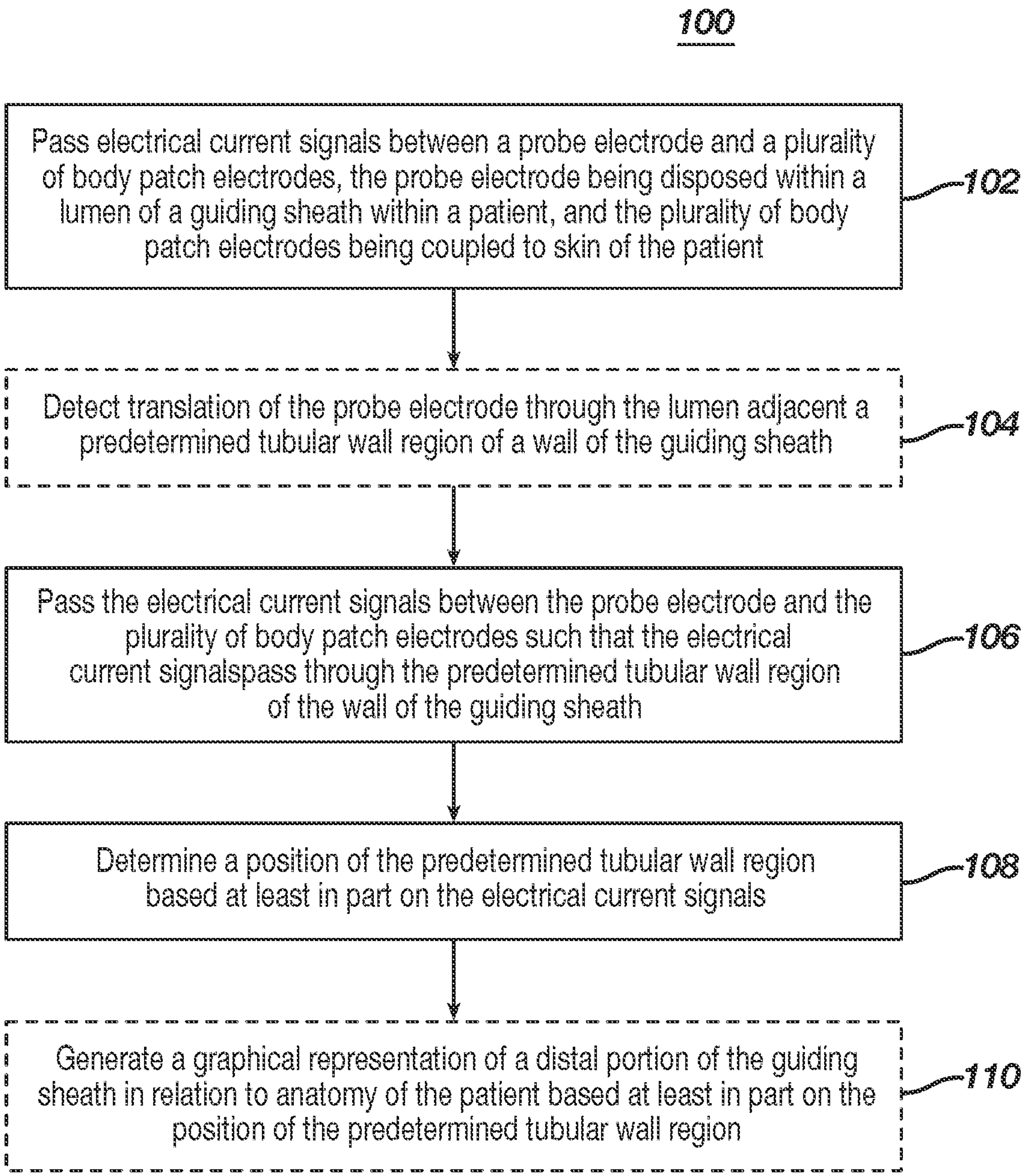
FIG. 7 is an illustration of a flow diagram of a method of impedance tracking a guiding sheath within a patient.

FIG. 7 is an illustration of a flow diagram of a method 100 of impedance tracking a guiding sheath within a patient. The method 100 can be carried out using the system illustrated in FIGS. 4A and 4B and the system 10 illustrated in FIG. 1, variations thereof, and alternatives thereto as understood by a person skilled in the art. The guiding sheath can be configured with features of the guiding sheath 40 illustrated herein, variations thereof, and alternatives thereto as understood by a person skilled in the art.

At block 102, electrical current signals can be passed between a probe electrode of a medical probe and a plurality of body patch electrodes while the probe electrode is disposed within a lumen of the guiding sheath within the patient and the plurality of body patch electrodes are in contact with skin of the patient. The probe electrode can be configured similar to any of the impedance-based tracking electrodes 26, 31, 35, 36, 37, 39 illustrated herein, variations thereof, and alternatives thereto as understood by a person skilled in the art. The plurality of body patch electrodes can be configured similar to the body patch electrodes 38 illustrated herein, variations thereof, and alternatives thereto as understood by a person skilled in the art. The medical probe can be configured similar to the catheter 14, dilator, medical probe with a dilator, other such medical probe as disclosed herein, variations thereof, and alternatives thereto as understood by a person skilled in the art. The electrical current signals can be passed between the body patch electrodes and the probe electrode by a control unit such as the control unit 56 illustrated in FIGS. 4A and 4B, a patient interface unit such as the PIU 30 illustrated in FIG. 1, variations thereof, and alternatives thereto as understood by a person skilled in the art.

At block 104, translation of the probe electrode through the lumen adjacent a predetermined tubular wall region of a wall of the guiding sheath is detected. The predetermined tubular wall region can be configured similar to the predetermined tubular wall region 62, 62*a-d* or conducting regions 45, 46 illustrated herein, variations thereof, and alternatives thereto as understood by a person skilled in the art.

At block 106, the electrical current signals between the probe electrode and the plurality of body patch electrodes can be passed such that the electrical current signals pass through the predetermined tubular wall region of the wall of the guiding sheath. The predetermined tubular wall region can include saline-filled pores through the wall of the guiding sheath, and the electrical current signals can be passed through the saline filled pores.

At block 108, a position of the predetermined tubular wall region can be determined based at least in part on the electrical current signals. A position of a distal end of the guiding sheath can be determined based at least in part on a predetermined distance between the predetermined tubular wall region and the distal end of the guiding sheath. Additionally, or alternatively, the electrical current signals can be passed through an electrically conductive band coupled to the wall of the guiding sheath at the predetermined tubular wall region. Additionally, or alternatively, the electrical current signals can be passed through electrically conductive rivets extending through the wall of the guiding sheath at the predetermined tubular wall region.

Additionally, or alternatively, the electrical current signals can be passed through electrically conductive fibers embedded in the wall of the guiding sheath at the predetermined tubular wall region. Position and orientation of the distal portion of the guiding sheath can be determined in relation to anatomy of the patient. Position of the distal portion of the guiding sheath can be determined without requiring an active position sensor on the guiding sheath. Position of the distal portion of the guiding sheath can be determined without requiring active electrical communication with the guiding sheath.

At block 110, a graphical representation of a distal portion of the guiding sheath in relation to anatomy of the patient can be generated based at least in part on the position of the conducting region.

The following clauses list non-limiting embodiments of the disclosure:

Clause 1. A guiding sheath comprising: a tubular shaft extending along a longitudinal axis between a proximal end and a distal end, the tubular shaft comprising a lumen therethrough and a tubular wall circumscribing the lumen such that a predetermined tubular wall region is configured to provide an electrically conductive path through the tubular wall of the tubular shaft, the predetermined tubular wall region being disposed proximate the distal end of the tubular shaft.

Clause 2. The guiding sheath of clause 1, the predetermined tubular wall region being disposed about 1 centimeter from the distal end and extending along the tubular shaft for about 1 millimeter to 2 millimeters.

Clause 3. The guiding sheath of clause 1 or 2, the predetermined tubular wall region being configured with pores sized to permit flow of saline from the lumen through the tubular wall of the tubular shaft.

Clause 4. The guiding sheath of any one of clauses 1-3, the predetermined tubular wall region comprising an electrically conductive band coupled to the tubular wall of the guiding sheath and configured to conduct electrical current between the lumen and an external environment of the tubular shaft.

Clause 5. The guiding sheath of any one of clauses 1-4, the predetermined tubular wall region comprising electrically conductive rivets extending through the tubular wall of the guiding sheath.

Clause 6. The guiding sheath of any one of clauses 1-5, the predetermined tubular wall region comprising electrically conductive fibers embedded in the tubular wall of the guiding sheath and configured to conduct electrical current between the lumen and an external environment of the tubular shaft.

Clause 7. The guiding sheath of any one of clauses 1-6, further comprising: a handle coupled to a proximal end of the tubular shaft and being configured to deflect a distal portion of the tubular shaft.

Clause 8. The guiding sheath of any one of clauses 1-7, further comprising: an irrigation port configured to provide irrigation fluid to the lumen.

Clause 9. The guiding sheath of any one of clauses 1-8, wherein the tubular shaft lacks an active position sensor.

Clause 10. The guiding sheath of any one of clauses 1-9, wherein the guiding sheath lacks an electrical port.

Clause 11. The guiding sheath of any one of clauses 1-10, wherein the tubular shaft comprises a plurality of predetermined tubular wall regions, including said predetermined tubular wall region, wherein each of the plurality of predetermined tubular wall regions are disposed a respective predetermined length from the distal end of the tubular shaft, and wherein each of the plurality of predetermined tubular wall regions provides an electrically conductive path through the tubular wall of the tubular shaft.

Clause 12. An impedance-based tracking system, comprising: a guiding sheath comprising a first tubular shaft comprising a lumen therethrough and a predetermined tubular wall region disposed approximate a distal end of the first tubular shaft, the predetermined tubular wall region configured to provide an electrically conductive path through the predetermined tubular wall region; a medical probe comprising a second tubular shaft configured to be translated through the lumen of the first tubular shaft and comprising a tracking electrode coupled to the second tubular shaft; a plurality of body patch electrodes configured to be in contact with skin of a patient; and a control unit configured to determine a position of the predetermined tubular wall region based at least in part on electrical signals between the tracking electrode and the plurality of body patch electrodes.

Clause 13. The impedance-based tracking system of clause 12, the control unit further being configured to determine a position of the distal end of the first tubular shaft of the guiding sheath based at least in part on the position of the predetermined tubular wall region.

Clause 14. The impedance-based tracking system of clause 12 or 13, the control unit further being configured to determine a position and orientation of a distal portion of the guiding sheath in relation to anatomy of the patient.

Clause 15. The impedance-based tracking system of any one of clauses 12-14, the predetermined tubular wall region being configured with pores sized to permit flow of saline from the lumen through a wall of the first tubular shaft.

Clause 16. The impedance-based tracking system of clause 15, further comprising: an irrigation source configured to provide saline through the lumen of the first tubular shaft and the pores.

Clause 17. The impedance-based tracking system of any one of clauses 12-16, the predetermined tubular wall region comprising an electrically conductive band coupled to a wall of the first tubular shaft and configured to conduct electrical current between the lumen and an external environment of the first tubular shaft.

Clause 18. The impedance-based tracking system of any one of clauses 12-17, the predetermined tubular wall region comprising electrically conductive rivets extending through a wall of the first tubular shaft.

Clause 19. The impedance-based tracking system of any one of clauses 12-18, the predetermined tubular wall region comprising electrically conductive fibers embedded in a wall of the first tubular shaft and configured to conduct electrical current between the lumen and an external environment of the first tubular shaft.

Clause 20. The impedance-based tracking system of any one of clauses 12-19, the predetermined tubular wall region being disposed about 1 centimeter to about 3 centimeters from a distal end of the first tubular shaft and extending over a length of about 1 millimeter to about 2 millimeters along the first tubular shaft.

Clause 21. The impedance-based tracking system of any one of clauses 12-20, the guiding sheath comprising a handle coupled to a proximal end of the first tubular shaft and being configured to deflect a distal portion of the first tubular shaft.

Clause 22. The impedance-based tracking system of any one of clauses 12-21, the guiding sheath comprising an irrigation port configured to provide irrigation fluid to the lumen.

Clause 23. The impedance-based tracking system of any one of clauses 12-22, wherein the first tubular shaft lacks an active position sensor.

Clause 24. The impedance-based tracking system of any one of clauses 12-23, wherein the guiding sheath lacks an electrical port.

Clause 25. The impedance-based tracking system of any one of clauses 12-24, wherein the first tubular shaft comprises a plurality of electrically conducting regions, including said electrically conducting region, wherein each of the plurality of electrically conducting regions are disposed a respective predetermined length from the distal end of the first tubular shaft, and wherein each of the plurality of electrically conducting regions provides an electrically conductive path between the lumen of the first tubular shaft and an external environment to the first tubular shaft.

Clause 26. The impedance-based tracking system of any one of clauses 12-25, the medical probe further comprising one or more electrodes configured to sense intracardiac electrogram signals.

Clause 27. The impedance-based tracking system of any one of clauses 12-26, the medical probe further comprising one or more electrodes configured to provide electrical signals for radio frequency ablation.

Clause 28. The impedance-based tracking system of any one of clauses 12-27, the medical probe further comprising one or more electrodes configured to provide electrical signals for ablation by irreversible electroporation.

Clause 29. The impedance-based tracking system of any one of clauses 12-28, the medical probe comprising a dilator.

Clause 30. A method of impedance tracking of a guiding sheath within a patient, the method comprising: passing electrical current signals between a probe electrode of a medical probe and a plurality of body patch electrodes, the probe electrode being disposed within a lumen of the guiding sheath within the patient, and the plurality of body patch electrodes being in contact with skin of the patient; and determining a position of a distal portion of the guiding sheath based at least in part on the electrical current signals.

Clause 31. The method of clause 30, further comprising: detecting translation of the probe electrode through the lumen adjacent to a predetermined tubular wall region of a wall of the guiding sheath.

Clause 32. The method of clause 31, further comprising: determining a position of the predetermined tubular wall region; and determining a position of a distal end of the guiding sheath based at least in part on a predetermined distance between the predetermined tubular wall region and the distal end of the guiding sheath.

Clause 33. The method of clause 31 or 32, further comprising: passing the electrical current signals between the probe electrode and the plurality of body patch electrodes such that the electrical current signals pass through the predetermined tubular wall region of the wall of the guiding sheath.

Clause 34. The method of clause 33, further comprising: passing the electrical current signals through saline-filled pores through the wall of the guiding sheath at the predetermined tubular wall region.

Clause 35. The method of clause 33 or 34, further comprising: passing the electrical current signals through an electrically conductive band coupled to the wall of the guiding sheath at the predetermined tubular wall region.

Clause 36. The method of any one of clauses 33-35, further comprising: passing the electrical current signals through electrically conductive rivets extending through the wall of the guiding sheath at the predetermined tubular wall region.

Clause 37. The method of any one of clauses 33-36, further comprising: passing the electrical current signals through electrically conductive fibers embedded in the wall of the guiding sheath at the predetermined tubular wall region.

Clause 38. The method of any one of clauses 30-37, further comprising: determining a position and orientation of the distal portion of the guiding sheath in relation to anatomy of the patient.

Clause 39. The method of any one of clauses 30-38, further comprising: determining the position of the distal portion of the guiding sheath without requiring an active position sensor on the guiding sheath.

Clause 40. The method of any one of clauses 30-39, further comprising: determining the position of the distal portion of the guiding sheath without requiring active electrical communication with the guiding sheath.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

What is claimed is:

1. An impedance-based tracking system, comprising:

a guiding sheath comprising a first tubular shaft comprising a lumen therethrough and a predetermined tubular wall region disposed approximate a distal end of the first tubular shaft, the predetermined tubular wall region configured to provide an electrically conductive path through the predetermined tubular wall region between the lumen of the first tubular shaft and an external environment to the first tubular shaft, the predetermined tubular wall region adjacent a second tubular wall region of the guiding sheath that is longer in length along a longitudinal axis of the guiding sheath than the predetermined tubular wall region;

a medical probe comprising a second tubular shaft configured to be translated through the lumen of the first tubular shaft and comprising a tracking electrode coupled to the second tubular shaft, the second tubular wall region comprising a higher electrical impedance than the predetermined tubular wall region such that electrical current more readily passes radially through the predetermined tubular wall region for impedance-based tracking of the tracking electrode when the tracking electrode is in axial alignment with the predetermined tubular wall region than when the tracking electrode is out of axial alignment with the predetermined tubular wall region;

a plurality of body patch electrodes configured to be in contact with skin of a patient; and a control unit configured to determine a position of the predetermined tubular wall region based at least in part on electrical signals between the tracking electrode and the plurality of body patch electrodes.

2. The impedance-based tracking system of claim 1, the control unit further being configured to determine a position of the distal end of the first tubular shaft of the guiding sheath based at least in part on the position of the predetermined tubular wall region.

3. The impedance-based tracking system of claim 1, the control unit further being configured to determine a position and orientation of a distal portion of the guiding sheath in relation to anatomy of the patient.

4. The impedance-based tracking system of claim 1, the predetermined tubular wall region being configured with pores sized to permit flow of saline from the lumen through a wall of the first tubular shaft.

5. The impedance-based tracking system of claim 1, the predetermined tubular wall region comprising an electrically conductive band coupled to a wall of the first tubular shaft and configured to conduct electrical current between the lumen and an external environment of the first tubular shaft.

6. The impedance-based tracking system of claim 1, the predetermined tubular wall region comprising electrically conductive rivets extending through a wall of the first tubular shaft.

7. The impedance-based tracking system of claim 1, the predetermined tubular wall region comprising electrically conductive fibers embedded in a wall of the first tubular shaft and configured to conduct electrical current between the lumen and an external environment of the first tubular shaft.

8. The impedance-based tracking system of claim 1, the predetermined tubular wall region being disposed about 1 centimeter to about 3 centimeters from a distal end of the first tubular shaft and extending over a length of about 1 millimeter to about 2 millimeters along the first tubular shaft.

9. The impedance-based tracking system of claim 1, the guiding sheath comprising a handle coupled to a proximal end of the first tubular shaft and being configured to deflect a distal portion of the first tubular shaft.

10. The impedance-based tracking system of claim 1, the guiding sheath comprising an irrigation port configured to provide irrigation fluid to the lumen.

11. The impedance-based tracking system of claim 1, wherein the first tubular shaft lacks an active position sensor.

12. The impedance-based tracking system of claim 1, wherein the guiding sheath lacks an electrical port.

13. The impedance-based tracking system of claim 1, wherein the first tubular shaft comprises a plurality of electrically conducting regions, including said electrically conducting region, wherein each of the plurality of electrically conducting regions are disposed a respective predetermined length from the distal end of the first tubular shaft, and wherein each of the plurality of electrically conducting regions provides the electrically conductive path between the lumen of the first tubular shaft and an external environment to the first tubular shaft.

14. The impedance-based tracking system of claim 1, the medical probe further comprising one or more electrodes configured to sense intracardiac electrogram signals.

15. The impedance-based tracking system of claim 1, the medical probe further comprising one or more electrodes configured to provide electrical signals for ablation.

16. The impedance-based tracking system of claim 1, the medical probe comprising a dilator.

* * * * *